United States Patent
Robins et al.

[11] Patent Number: 5,713,941
[45] Date of Patent: Feb. 3, 1998

[54] PPARATUS FOR INDUCING WHOLE BODY HYPERTHERMIA AND METHOD FOR TREATMENT UTILIZING SAID WHOLE BODY HYPERTHERMIA INDUCING APPARATUS

[75] Inventors: H. Ian Robins, Madison, Wis.; Justin D. Cohen, Denver, Colo.

[73] Assignee: Cancer Research Institute, New York, N.Y.

[21] Appl. No.: 53,883

[22] Filed: Apr. 27, 1993

[51] Int. Cl.$^6$ .................................................. A61F 7/00
[52] U.S. Cl. ............................ 607/96; 607/104; 126/204
[58] Field of Search .......................... 607/96, 104–107; 600/2; 165/169; 126/204

[56] References Cited

U.S. PATENT DOCUMENTS

| | | | |
|---|---|---|---|
| 1,622,903 | 3/1927 | Cox | 607/104 |
| 3,517,732 | 6/1970 | Brebant | 165/169 |
| 4,459,468 | 7/1984 | Bailey | 607/104 |
| 5,184,612 | 2/1993 | Augustine | 607/104 |
| 5,197,946 | 3/1993 | Slevert et al. | 600/9 |
| 5,330,519 | 7/1994 | Mason et al. | 607/104 |

FOREIGN PATENT DOCUMENTS

| | | | |
|---|---|---|---|
| 1352142 | 5/1974 | United Kingdom | 607/104 |
| 2254004 | 9/1992 | United Kingdom | 607/96 |

*Primary Examiner*—Robert L. Nasser
*Attorney, Agent, or Firm*—Felfe & Lynch

[57] ABSTRACT

The present invention provides an improved whole body hyperthermia apparatus for raising the body temperature of a patient, said apparatus emitting radiant heat from a surface heated by a fluid. The present invention also provides an improved method for treating a cancer patient, said method comprising administering an anti-neoplastic agent to the cancer patient undergoing whole body hyperthermia under less stressful and more effective conditions with the improved whole body hyperthermia apparatus.

8 Claims, 4 Drawing Sheets

APPARATUS FOR INDUCING WHOLE BODY HYPERTHERMIA AND METHOD FOR TREATMENT UTILIZING SAID WHOLE BODY HYPERTHERMIA INDUCING APPARATUS

FIELD OF THE INVENTION

The subject invention relates to an improved apparatus for inducing whole body hyperthermia and an improved method for treating a cancer patient with an anti-neoplastic (i.e., therapy) agent in combination with the improved whole body hyperthermia inducing apparatus.

BACKGROUND OF THE INVENTION

Hyperthermia has been applied to various diseases, including cancer, since ancient times. During the past two decades laboratory data have provided evidence to support the clinical use of hyperthermia in the treatment of neoplastic diseases. The potential of hyperthermia as a treatment modality for cancer was first predicted following observations that several types of cancer cells were more sensitive to temperatures in excess of 41° C. than were their normal cell counterparts (Giovanella, B. D., et al. *Cancer Res.* 33:2568–2578 (1973), Robins, H. I., et al. *Cancer Res.* 43:4951–4955 (1983) and Flentje, M., et al. *Cancer Res.* 44:1761–1766 (1984)).

Beyond those studies, there is preclinical evidence as well as clinical suggestions that hyperthermia can be synergistically combined with drugs such as anesthetic agents, (Yatvin, M. B., et al. *Science* 205:195–196 (1979), Robins, H. I., et al. *Cancer Res.* 43:3187–3191 and Robins, H. I., et al. *Cancer* 54:2831–2835 (1984) chemotherapeutic agents, (Cohen, J. D., et al. *Cancer Letters* 44:205–210 (1989), Robins, H. I., et al. *Cancer Res.* 48:6587–6592, Robins, H. I., et al. *AACR abs.* 31 (1990) and Robins, H. I., et al. *Cancer Res.* 44:4878–4883 (1984), interferons (Robins, H. I., et al. *Cancer Res.* 44:4878–4883 (1984), Groveman, D. S., et al. *Cancer Res.* 44:5517–5521 (1984) and Robins, H. I., et al. *Cancer Res.* 49:1609–1615 (1989), as well as radiation (Li, G., et al. *Radiat. Res.* 67:491–501 (1976), Mivechi, N. F., et al. *Cancer* 51:38–43 (1983), Steeves, R., et al. *Int. J. Radiation Biology* 52:935–947 (1987), Robins, H. I., et al. *Int. J. Radiat. Oncol. Biol. Phys.* 15:427–531 (1988) and Robins, H. I., et al. *Int. J. Radiat. Oncol. Biol. Phys.*, 18:909–920 (1990). Laboratory research has repeatedly shown antitumor activity by hyperthermia (Robins, H. I., B. C. Decker, *Philadelphia, Pa. pgs.* 371–373 (1988)).

The existing radiant heat technology for inducing whole body hyperthermia utilizes radiant heat energy emitted from a metal cylinder covered with an electrical heating coil. This device, used for the past ten years or so, is described in U.S. Pat. No. 4,501,275. There is one major difference, however, between the device described in the '275 patent and the device that has been in use. The device disclosed in the '275 patent does not have means for humidifying the air surrounding the patient whereas the device that has been in use does.

The aforementioned radiant heat emitting device which has means for humidifying the air surrounding the patient has been used extensively in clinical testing to induce whole body hyperthermia in cancer patients (Robins, H. I., et al. *Cancer Res.* 45:3937–3944 (1985), Robins, H. I., et al. *IEEE/Engineering in Medicine and Biology Society, Chicago,* September (1985) and Robins, H. I. et al., in *J. Overgaard* (ed), Taylor and Francis, London and Philadelphia, pg. 269–272 (1984)). For example, this device has been used to induce whole body hyperthermia in cancer patients undergoing treatment with interferon (Robins, H. I., et al. *Cancer Res.* 49:1609–1615 (1989), regional radiotherapy for non-small cell lung cancer (Robins, H. I., et al. *Int. J. Radiat. Oncol. Biol. Phys.* 15:427–531 (1988), chemotherapy (Robins, H. I., et al. *Cancer Res.* 48:6587–6592 (1988) and Robins, H. I., et al. *AACR abs.* 31 (1990), total body irradiation (TBI) for low grade neoplasms, (Robins, H. I., et al. *Int. J. Radiat. Oncol. Biol. Phys.*, 18:909–920 (1990), and ablative TBI (Robins, H. I., et al. *The Cancer Journal* 1:180–183 (1986). While this device represents an improvement over prior designed whole body hyperthermia inducing apparatuses, it still contains a number of drawbacks.

First, because the radiant heat source is electrical, i.e., heating cables, regulation of the temperature is difficult to control and calibration of the machine is difficult and time consuming. The problem of calibrating the radiant heating device stems from the limited capability to determine the actual surface radiating temperature of the heating cable.

Second, because the radiating surface is smooth, the overall efficiency of radiant heat exchange is sub-optimal. Consequently, the device must be operated at a relatively high temperature for a relatively longer period of time, thereby causing patient discomfort and possibly cardiac stress.

Thus, there exists a need for a whole body hyperthermia device which is easy to calibrate, demonstrates superior temperature stability, can operate at lower surface temperatures, and has a high efficiency of radiant heat exchange.

SUMMARY OF THE INVENTION

The present invention provides an improved whole body hyperthermia apparatus which is easy to calibrate, demonstrates superior temperature stability, operates at lower surface temperatures, and has a high efficiency of radiant heat exchange.

More specifically, the present invention provides an improved whole body hyperthermia apparatus for raising the body temperature of a patient up to a maximum of 41.8° C. in a humidified environment including means to emit radiant heat from a surface, the improvement comprising having radiant heat emitted from said surface heated by a fluid.

The present invention also provides an improved method for administering an anti-neoplastic agent to a cancer patient undergoing whole body hyperthermia, wherein prior to, during, or after said patient is administered said anti-neoplastic agent, the body temperature of said patient is raised up to a maximum of about 41.8° C. in a humidified environment, the improvement which comprises exposing said patient to radiant heat emitted from a scalloped surface heated by a fluid.

DETAILED DESCRIPTION OF THE INVENTION

Figure 1:
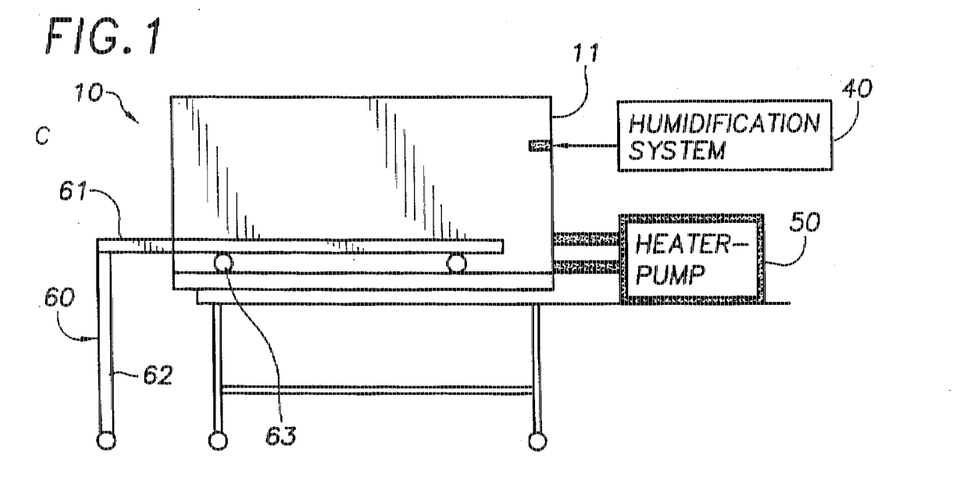
FIG. 1 is a schematic elevation of the apparatus.

FIG. 1 shows apparatus 10 of the present invention for inducing whole body hyperthermia in the patient. Apparatus 10 includes a cylindrical housing 20 forming a tubular chamber 21 mounted on a framework 30.

The cylindrical housing 20 comprises an outer layer of insulation 22, a middle layer comprising four coiled metal tubes 23, serially arranged, each having a fluid intake 24 and outlet 25, and an inner layer of high temperature paint 26 which facilitates maximum emissivity.

Humidification system 40 provides sterile humidified mist to the tubular chamber 21 by means of inlet ports (not shown) provided on the rear wall 11 of the apparatus.

Figure 5:
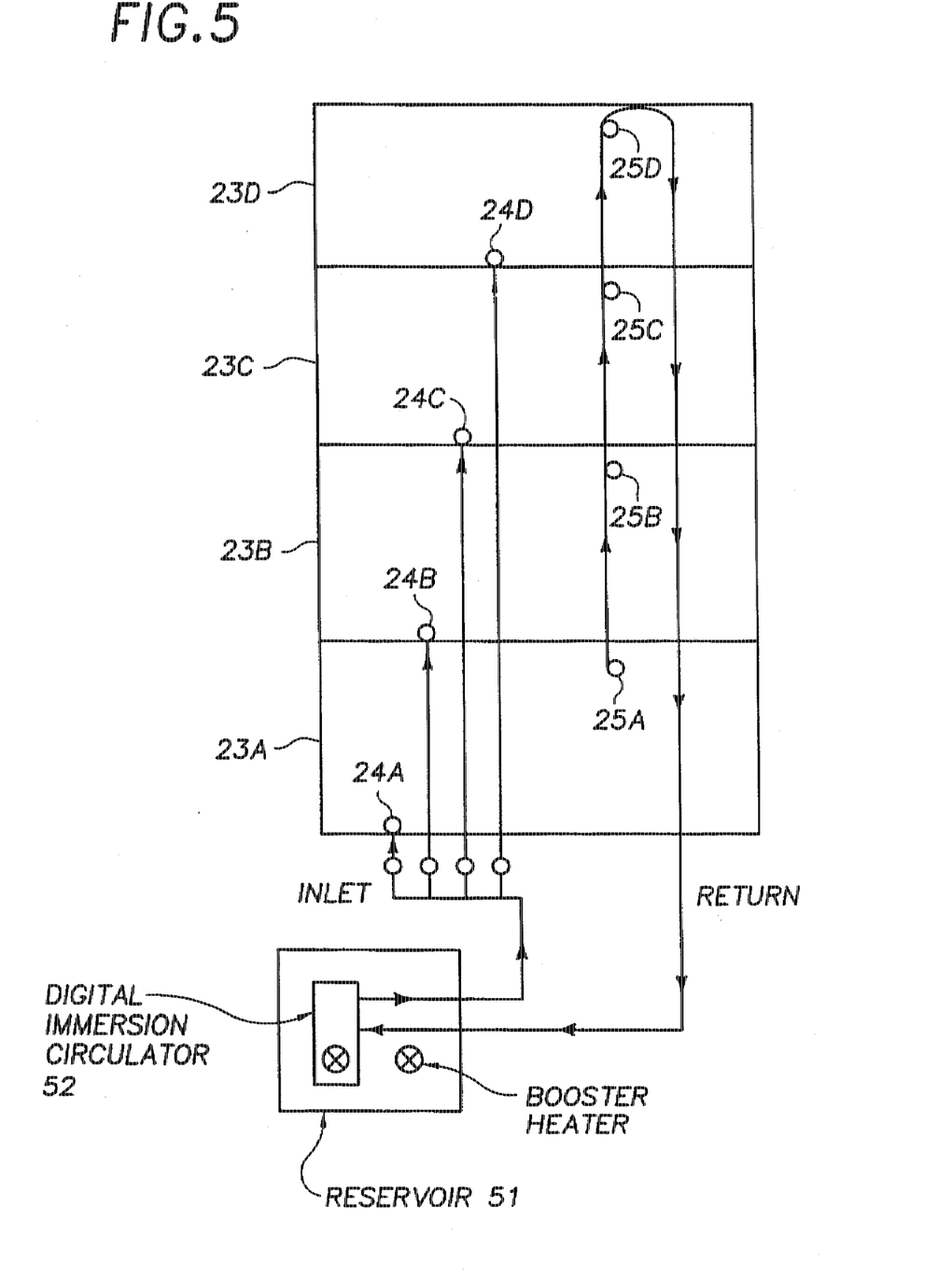
FIG. 5 is a schematic of the fluid flow.
Figure 6:
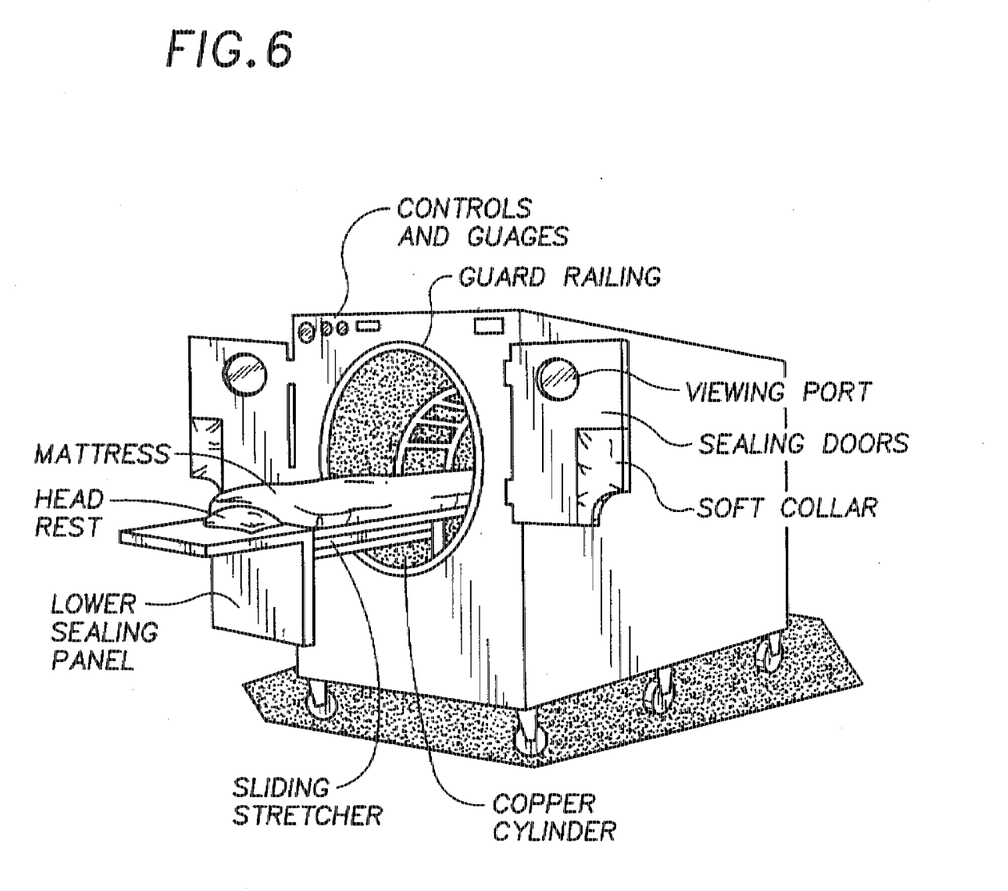
FIG. 6 is a perspective view of a prior art radiant heating device

The liquid circulates in a counter current distribution system through each of the four serially arranged side-by-side coils 23 by means of an inflow manifold 24A, 24B, 24C and 24D and an outflow manifold 25A, 25B, 25C and 25D. FIG. 5 is a plumbing schematic illustrating the liquid counter current distribution system between the various sections of copper coil.

Fluid in the reservoir 51 is heated to the desired temperature and then pumped by an immersion circulator 52 to the intake manifold where the fluid enters to each of the four serially arranged coils 23 through individual intakes 24A, 24B, 24C and 24D of the intake manifold. The fluid circulates through each of the serially arranged coils and then exits through each of the respective outlets of the outtake manifold 25 where the fluid journeys to the reservoir 51. This is a continuous process.

Thus, heated fluid enters manifold 24A of coil 23A and exits thru outlet 25A. In the next coil, 23B, heated fluid enter manifold 24B and exits outlet 25B, and so on for the remaining coils 23C and 23D. The outlets 25A, 25B, 25C, and 25D feed a common line for returning fluid to the reservoir 51.

Figure 2:
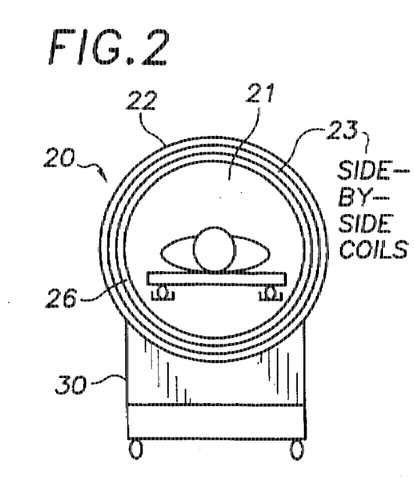
FIG. 2 is an end view of the apparatus in use.
Figure 3:
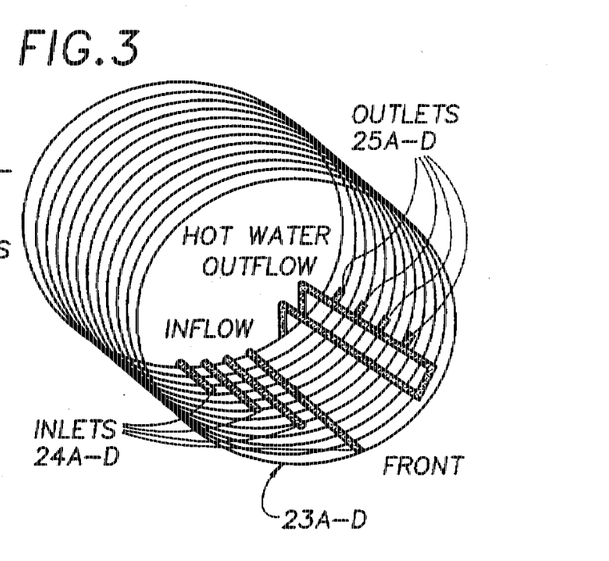
FIG. 3 is a schematic perspective of the coil.
Figure 4:
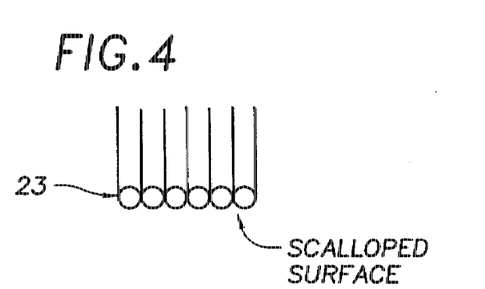
FIG. 4 partial sectional view of the turns of the coil.

Cart 60 is comprised of a flat stretcher 61 supported by legs 62, only one of which is depicted. Bearings 63 provide means to slide the cart inside the apparatus 10.

A patient to be treated lies on the stretcher which is slid into the tubular chamber. A non-conductive plastic netting is provided inside the heating chamber to prevent patient contact with the inner heat radiating surface of the chamber. An industry standard 40 watt light bulb is incorporated into the rear wall of the device to maximize observations of the patient during treatments. Two non-thermally conductive plexiglass doors are provided at the head of the apparatus. These doors allow the patients head to remain outside the heating chamber at all times. A soft collar is incorporated into the door design which fits around the neck of the patient, thereby, creating a closed system.

The digital immersion circulator is set to a desired temperature approximately 12 hours prior to a patient treatment. The fluid temperature is maintained and monitored by reading the temperature off the digital immersion calculator.

During the heating phase, the hyperthermia inducing apparatus is kept at a set temperature determined directly by the fluid temperature produced by the digital immersion circulator. The temperature setting of the circulator should not exceed 65° C., and is set, preferably, at 60° C.±0.5° C. for standard treatments. The temperature range that the hyperthermia inducing apparatus can produce in a patient is from 37° C. up to 42° C. Most preferably, the temperature of the patient is heated to 41.8° C. The temperature of the patient is monitored using procedures well known in the art.

Following the heating phase, i.e., after the patient achieves target temperature, the patient is removed from the hyperthermia apparatus by extending the stretcher and covering the patient with a vapor/heat barrier in accordance with procedures well known to those of ordinary skill in the art. See Robins, et al., *Cancer Research*, 45:3937–3944 (1985), the disclosure of which is incorporated in its entirety by reference. When the patient is at peak temperature, e.g., 41.8° C., it is the patient's increased metabolic rate which maintains the body temperature, not the hyperthermia inducing apparatus.

In a preferred embodiment, the core of the whole body hyperthermia inducing device consists of a 200 by 61 cm coil constructed from copper tubing (⅝" outer diameter: type L ½" inner diameter wall thickness 0.040"). The coil forms a scalloped surface, thereby increasing the surface area of the radiant heat emitting surface by a factor of 1.57 compared to a smooth surface. The coil is divided into four subsidiary sections (each of which consists of 32 turns developed from three 100 foot sections of tubing) joined end to end. The four component sections have separate fluid intakes and a common fluid outlet. The metal to metal contact between each loop of coil along with the inflow and outflow designed effectively produces a counter current heat distribution system. Insulation lining the outer surface and ends of the coil also contribute to the excellent heat constancy of the system. The minimal loss of heat and the other aforementioned design features reduce any potential temperature gradient along the coil to negligible level. The mass of fluid and copper tubing as well as the comprehensive insulation give the system considerable heat "inertia" resulting in exceptional temperature stability.

The surface of the copper coils are painted with a high temperature-high emissivity finish i.e., flat black, in order to maximize radiant heat exchange between the coil surface and the patient.

Both the heating and pumping of the fluid is accomplished by a Neslab model EX-810D immersion circulator, (Nexlab Instruments, Newington, N.H.). This immersion circulator has an 800 watt heater (115 volts, 60 HZ, 11 Amps) with a temperature stability of ±0.1° C. and a pumping rate of 12 liters per minute (17" head).

A humidification system based on the use of two Devilbiss 65 ultrasonic nebulizers (Devilbiss Company, Somerset, Pa.); two inlet ports for sterile humidified mist are provided on the rear wall of the hyperthermia apparatus produces humidities in the range of 90–100%, which are adequate to prevent significant evaporative heat losses. The percentage of humidity is not critical to the performance of the hyperthermia inducing apparatus. Effectively, after the first ten minutes, the humidity is 100%.

The hyperthermia inducing apparatus has a general housing of stainless steel sheeting which is supported by a stainless steel frame. The design is such that it allows for easy cleaning and sterilization.

The subject hyperthermia inducing apparatus exhibits a superior temperature stability due to the heating inertia in the specific heat of the fluid, namely water and most preferably, oil, and the counter current fluid flow. The superior temperature stability effectively eliminates convection currents within the tubular chamber.

In addition, the net effect of the increased surface area of the radiating surface is to increase the overall efficiency of radiant heat exchange, thereby decreasing heating times. Faster heating times results in increased patient comfort as well as decreased thermal tolerance. The increased surface area of the radiating surface also allows for a decrease of a few degrees in the surface radiating temperature of the WBH at operational temperatures, resulting in an increase in subject comfort during the heating phase of a WBH treatment.

The hyperthermia inducing apparatus is appropriate for a multimodality approach to treating systemic cancers. Using techniques well known in the art, as per Robins, H. I., et al. *Cancer Res.* 44:4878–4883 (1984), Robins, H. I., et al. *Cancer Res.* 48:6587–6592, Robins, H. I., et al. *Cancer Res.* 49:1609–1615 (1989) Robins, H. I., et al. *Int. J. Radiat. Oncol. Biol. Phys.* 15:427–531 (1988), (Robins, H. I., et al. *Cancer Res.* 45:3937–3944 (1985), the contents of which are incorporated herein in there entireties by reference, anti-neoplastic agents are administered to the cancer patient prior to, during, or after the patient has undergone whole body hyperthermia in the subject apparatus. See Robins, H. I., et al. *AACR abs.* 31 (1990); Robins et al., "Whole Body Hyperthermia: Biological and Clinical Aspects," Springer Verlag, Berlin, Germany, 1–84 (1992), the contents of which are incorporated herein in there entireties by reference. The term "anti-neoplastic agents" includes, but is not limited to total body radiation, local radiation, chemotherapeutic agents such as methotrexate and cis-platinum compounds, and biological response modifiers, e.g., interferons and tumor necrosis factor.

The hyperthermia inducing apparatus is also useful for treatment of collagen vascualar diseases such as arthritis and psoriasis and for treating hypothermia. In addition, the hyperthermia inducing apparatus is also useful for enhancing the effects of labilizers such as the anaesthetic agents lidocaine and thiopentyl.

EXAMPLE I

1. Anesthesia

Seven Dogs were fasted for 18 hours immediately prior to general anesthesia for the whole body hyperthermia treatments. Atropine (0.04 mg/kg IM), diazepam (0.04 mg/kg IM), and fentanyl (10 mcg/kg IM) were given as premedication, 20 to 30 minutes prior to induction of general anesthesia with an intravenous bolus of thiopental (5 mg/kg IV) and fentanyl (0.4 mg/kg IV). Atracurium (Tracurium, Burroughs Wellcome Co., Research Triangle Park, N.C. 27709, USA), a nondepolarizing neuromuscular blocking agent was given as a bolus (0.4 mg/kg IV) to paralyze the muscles of respiration. Ventilation was maintained with a positive-pressure mechanical ventilator (15 to 20 ml/kg tidal volume to 20 to 25 breaths per minutes) (Edco Model 821 large animal ventilator, Edco Scientific, Inc., Chapel Hill, N.C. 27514, USA). Anesthesia and paralysis were maintained with a continuous infusion of fentanyl (1.0 mcg/kg/minute) and atracurium (8.5 mcg/kg/minute). Thiopental boluses (2.5 mg/kg IV up to a total dose of 30 mg/kg) were given as needed, based on assessment of indirect blood pressure, heart rate, and pupillary dilation. Vital signs were recorded every 5 minutes. The level of neuromuscular blockade was assessed by carpal twitch response to indirect ulnar nerve train-of-four stimulation (Life Tech Inc., Houston, Tex., USA). Intravenous fluids, 5% dextrose in water (D5W) (Baxter Healthcare Corp., Deerfield, Ill. 60015, USA) were administered at 10 ml/kg/hour throughout the experiment. At the end of the treatment, the fentanyl-atracurium infusion was discontinued and atropine (0.05 mg/kg IM) was administered followed by neostigmine (0.05 mg/kg IV). Upon return of respiratory muscle function, mechanical ventilation was discontinued.

2. Physiological Monitoring

Heart rate and indirect systolic, diastolic, and mean systemic arterial pressures (Dinamap, Critikon Inc., Tampa, Fla. 33630, USA) were monitored continuously and recorded every 10 minutes. A lead II electrocardiogram (Strathem Model SM 1057 monitor) was continuously monitored. A pulse oximeter (Ohmeda, Boulder, Colo., USA) placed on the distal aspect of the tongue continuously monitored arterial oxygen percent saturations which were recorded every 10 minutes.

3. Temperature Probes

After the dogs were anesthetized, prior to being moved into the hyperthermia inducing apparatus device (RHD), thermocouples (Bailey Thermalert TH-6, Sensor Tek Inc., Clifton, N.J., USA) were strategically placed. The rectal probe was inserted halfway up the descending colon. Position was confirmed by abdominal palpation. Bone marrow temperature probes were placed in the wing of the ilium, right proximal humerus, and the right medial proximal tibia. The bone marrow sites were aseptically prepared by clipping, cleaning with chlorhexidine (Nolvasan, Fort Dodge Laboratories, Inc., Fort Dodge, Iowa 50501, USA), and surgical prep (Prepodyne Povidone Scrub, AMSCO, Medical Products Division, Division of American Sterilizer Co., Erie, Pa. 16514, USA). A 1.5 to 2-cm skin incision and blunt dissection of the overlying subcutaneous and muscle tissue exposed the bone sites. A sterile 4-mm trephine bone biopsy instrument (Richards Manufacturing Co., Inc., Memphis, Tenn. 38116, USA) removed a core of bone 1.5 to 2.0 cm deep. A temperature probe previously sterilized and immersed in alcohol was then firmly wedged into the bone marrow. All temperature probes were secured to the dog with adhesive tape.

Thermocouples were used to measure the temperatures in the experiments. Temperatures were monitored with three 5-probe switchboxes connected in series and a thermocoupler reader which displayed temperatures in 0.1° C. increments. The thermometry system was calibrated against a platinum-resistant temperature device (Instrulab, Inc., Dayton, Ohio, USA). Calibration data were used to correct the experimental temperature measurements recorded. The overall accuracy of the thermometry system was ±0.1° C.

4. Whole-Body Hyperthermia Treatment Procedure

After confirming accurate placement of temperature probes and physiological monitoring sensors, the dog was slid on a stretcher into the prewarmed hyperthermia inducing device.

The hyperthermia treatment consisted of a heating phase, plateau phase at target temperature, and a cooling phase. During the heating phase (75–100 minutes), the dog was in the hyperthermia inducing device. The plateau phase was defined as the target rectal temperature (41.8° C.) maintained for 60 minutes. Upon reaching the target rectal temperature, the dog was covered with a heat-reflective blanket and removed from the hyperthermia inducing device. The nonlinearly increased basal metabolic rate of the dog at target temperature was equal to the heat losses from the covered dog, thus resulting in stable rectal temperature with the covered dog totally outside the heating chamber of the hyperthermia inducing device. When necessary, temperature regulation was performed by exposing parts of the dog to allow sufficient heat loss if the core temperature continued to rise. If the core temperature decreased, then the covered dog was partially moved into the hyperthermia inducing device, reducing conductive heat loss. Treatment time was defined as the elapsed time at plateau temperature. (i.e., 60 minutes)

At the conclusion of the plateau phase, the dog was uncovered and actively cooled by moistening the skin with water or alcohol to allow for evaporative cooling and by exposing the dog to room air to maximize radiant heat loss. The cooling phase to a core temperature of about 38° to 39° C. was 40 to 50 minutes. Following the cooling phase, animals were sacrificed. At that point, dissections were performed to verify the placement of temperature probes. A typical whole body hyperthermia treatment session lasted a total of 4 to 6 hours.

5. Temperature Monitoring

Temperatures were recorded from the rectum and bone marrows (wing of the ilium, right proximal humerus, and the right medial proximal tibia) for each dog. Temperature readings were recorded from all probes every 10 minutes throughout the procedure, starting with baseline values obtained prior to the dog being inserted into the hyperthermia inducing apparatus.

6. Statistical Analysis

Temperature data obtained from the rectum, and ilial, humeral, and tibial bone marrows were corrected based on calibration data. Analysis of the calibration data demonstrated the thermocouple temperature probes were well within the manufacturer's stated accuracy. The data were compared using an analysis of variance for repeated measures with statistical significance determined at $p<0.001$. The difference between the corrected rectal temperature and the corrected ilial, humeral, and tibial bone marrow temperatures (i.e., bone marrow minus rectum) were calculated for each time period during the plateau phase. These derived values were referred to as relative ilial, humeral, and tibial bone marrow temperature, respectively. Comparisons between temperatures at each site (i.e. rectum and bone marrows) were made with Tukey's Studentized range test with statistical significance determined at $p<0.001$.

Although a true thermal "dose" has not been determined, for purposes of comparison, the corrected bone marrow and rectal time-temperature profiles during WBH plateau phase were converted to equivalent-minutes at 43° C. ($t_{43}$) by the method of Sapareto and Dewey, Sapareto et al., *Int. J. Radiat. Oncol. Biol. Phys.* 10: 787–800 (1984).

$$t_{43} = \Sigma_{t=0}^{t=60} (\delta t) R^{(43-T)}$$

where $t_{43}$ is the equivalent time at 43° C., T is the average temperature (°C.) during time $\delta t=10$ minutes and $R=0.25$ when $T \geq 42.5°$ C. and 0.5 when $T>42.5°$ C. Mean $t_{43}$ values were calculated for the rectum and ilial, humeral, and tibial bone marrows and compared by Student's t-test.

7. RESULTS

The hyperthermia inducing apparatus induced a readily reproducible heating curve during WBH in the seven dogs. The time to target temperature (41.8° C.) was 85 to 100 minutes. The variation in time to target temperature was predominately due to the dog's starting core temperature at the time that physiological and temperature monitoring instruments had been secured. The rate of heating was 0.058°±0.002° C. per minutes (mean±standard error of the mean [SEM]). The core temperature in six dogs remained elevated in a stable plateau phase for 60 minutes until active cooling was initiated. In one treatment, however, the rectal temperature of the dog decreased below the 41.8° C. target, necessitating placement of the dog back into the RHD. During the plateau phase of 41.8° C., a mean rectal temperature of 41.9°±0.06° C. was maintained with a range of 41.4° to 42.2° C.

Figure 7:
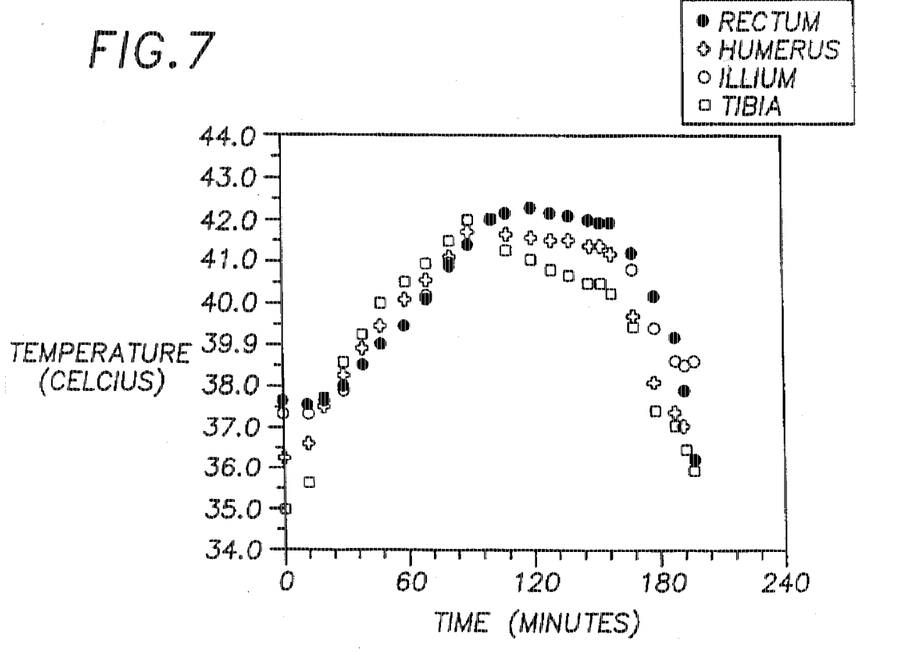
FIGS. 7 and 8 are time temperature profiles of dogs treated with the subject hyperthermia inducing apparatus.
Figure 8:
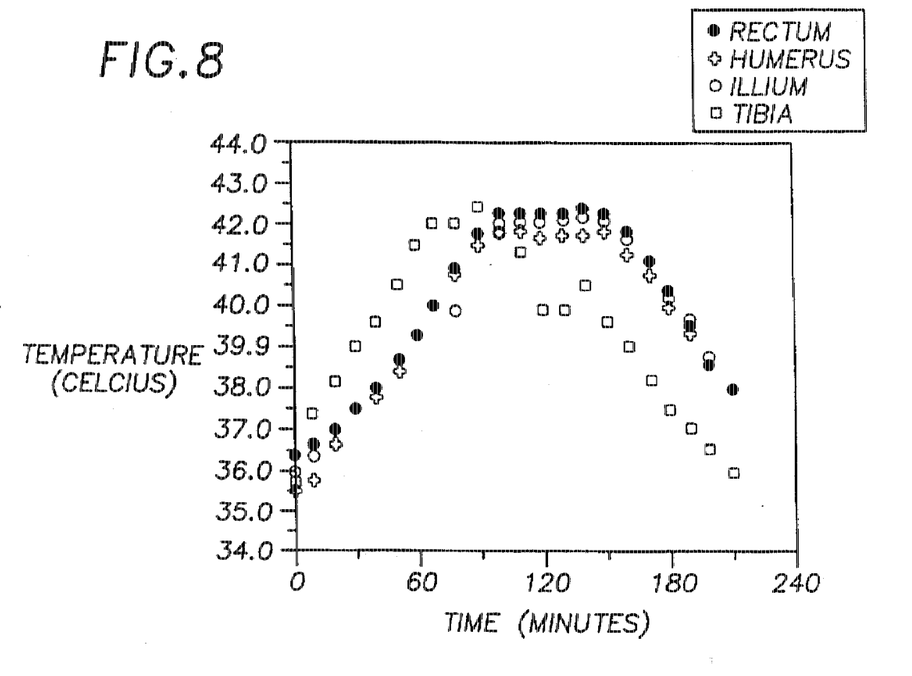

The time-temperature profiles of the rectum and the bone marrow sites (ilium, humerus, and tibia) during WBH, along with the relative bone marrow temperatures (bone marrow minus rectum) during plateau are given for two representative dogs in FIGS. 7 and 8.

It is believed that other embodiments may be incorporated into the present invention without departing from the spirit and scope of the invention. It is not intended that the present invention be limited to only the described embodiments. Modification of these embodiments will be recognized by those skilled in the art. Rather, the invention should be circumscribed by the scope of the appended claims.

We claim:

1. Whole body hyperthermia apparatus for raising the body temperature of a patient in a humidified environment comprising:

(a) cylindrical chamber means for enclosing the full length of said patient, except for the patient's head;

(b) means for humidifying said chamber means;

(c) a plurality of serially arranged, side-by-side coil means having a high emissivity finish for efficiently and reproducibly heating said patient up to a maximum of 41.8° C., each of said coil means having separate fluid inlet and fluid outlet wherein the outlet of one coil means is adjacent to the inlet of the next side-by-side coil means; and (d) heated reservoir means for simultaneously circulating heated fluid through each of said coil means.

2. Apparatus of claim 1 wherein said high emissivity finish is flat black paint.

3. Apparatus of claim 1 wherein said reservoir means includes means to limit the temperature of the heated fluid to 65° C.

4. Apparatus of claim 1 wherein said side-by-side coils means form a scalloped surface which carries said high emissivity finish.

5. Apparatus of claim 4 wherein said scalloped surface has a surface area 1.57 times greater than a non-scalloped, smooth surface.

6. Apparatus of claim 1 wherein said heated fluid is water.

7. Apparatus of claim 1 wherein said heated fluid is oil.

8. Apparatus of claim 1 wherein coils means are copper.

* * * * *

UNITED STATES PATENT AND TRADEMARK OFFICE
CERTIFICATE OF CORRECTION

PATENT NO. : 5,713,941
DATED : February 3, 1998
INVENTOR(S) : Robins, et. al.

It is certified that error appears in the above-identified patent and that said Letters Patent is hereby corrected as shown below:

Title page, item [54], in the title, line 1, "PPARATUS" to --APPARATUS--.

In the drawings, sheet 4, figures 7 and 8, change "(CELCIUS)" to -- (CELSIUS) --; and change "ILLIUM" to -- ILIUM --.

In column 1, lines 47-48, change "B.C. Decker" to -- *B.C. Decker* --; and change "*Philadelphia, Pa. pgs.*" to -- Philadelphia, Pa. pgs. --.

In column 1, line 65, change "*Chicago*" to -- Chicago --.

In column 3, line 17, delete "serially arranged".

In column 3, line 18, delete "23" and insert therefor -- 23A, 23B, 23C and 23D --.

In column 3, line 26, delete "23" and insert therefor -- 23A, 23B, 23C and 23D --.

UNITED STATES PATENT AND TRADEMARK OFFICE
CERTIFICATE OF CORRECTION

PATENT NO. : 5,713,941
DATED : February 3, 1998
INVENTOR(S) : Robins, et. al.

It is certified that error appears in the above-identified patent and that said Letters Patent is hereby corrected as shown below:

In column 3, line 50, change "patients" to -- patient's --.

In column 5, line 14, change "there" to -- their --.

In column5, line 21, change "there" to -- their --.

In column 5, line 28, change "vascualar" to -- vascular --.

In Claim 1, column 8, line 29, change "fall" to -- full --.

Signed and Sealed this

Thirtieth Day of November, 1999

Attest:

Attesting Officer

Q. TODD DICKINSON

Acting Commissioner of Patents and Trademarks